(12) United States Patent
Liu et al.

(10) Patent No.: US 11,761,865 B2
(45) Date of Patent: Sep. 19, 2023

(54) ROCK TRUE TRIAXIAL DYNAMIC COMPRESSION-SHEAR TEST EQUIPMENT AND METHOD UNDER DEEP COMPLEX STRUCTURE CONDITIONS

(71) Applicants: DEEP WELL MINING LABORATORY BRANCH OF SHANDONG GOLD MINING TECHNOLOGY Co., Ltd, Laizhou (CN); Xiwei Zhang, Liaoning (CN)

(72) Inventors: Huanxin Liu, Shandong (CN); Yumin Chen, Shandong (CN); Jianbo Wang, Laizhou (CN); Xiwei Zhang, Liaoning (CN); Shuhao Du, Laizhou (CN); Kuikui Hou, Laizhou (CN); Yang Liu, Laizhou (CN); Guilin Li, Laizhou (CN); Mingde Zhu, Laizhou (CN); Xi Wang, Laizhou (CN); Qinzheng Wu, Laizhou (CN)

(73) Assignees: DEEP WELL MINING LABORATORY BRANCH OF SHANDONG GOLD MINING TECHNOLOGY CO., LTD, Shandong (CN); Xiwei Zhang, Liaoning (CN)

( * ) Notice: Subject to any disclaimer, the term of this patent is extended or adjusted under 35 U.S.C. 154(b) by 423 days.

(21) Appl. No.: 17/265,999

(22) PCT Filed: Dec. 31, 2020

(86) PCT No.: PCT/CN2020/142067
§ 371 (c)(1),
(2) Date: Feb. 4, 2021

(87) PCT Pub. No.: WO2022/134187
PCT Pub. Date: Jun. 30, 2022

(65) Prior Publication Data
US 2022/0196527 A1 Jun. 23, 2022

(30) Foreign Application Priority Data

Dec. 23, 2020 (CN) ............................ 202011538588

(51) Int. Cl.
*G01N 3/10* (2006.01)
*G01N 3/24* (2006.01)
(Continued)

(52) U.S. Cl.
CPC ................. *G01N 3/12* (2013.01); *G01N 3/36* (2013.01); *G01N 2203/0019* (2013.01); *G01N 2203/0048* (2013.01); *G01N 2203/0256* (2013.01)

(58) Field of Classification Search
CPC .... G01N 3/12; G01N 3/36; G01N 2203/0019; G01N 2203/0048; G01N 2203/0256;
(Continued)

(56) References Cited

U.S. PATENT DOCUMENTS

| 5,421,205 A | 6/1995 | Pohl | |
|---|---|---|---|
| 2011/0132099 A1* | 6/2011 | Secq | E21B 47/12 73/845 |

(Continued)

FOREIGN PATENT DOCUMENTS

| CN | 102288486 A | 12/2011 |
|---|---|---|
| CN | 103698201 A | 4/2014 |

(Continued)

*Primary Examiner* — Brandi N Hopkins
(74) *Attorney, Agent, or Firm* — Muncy, Geissler, Olds & Lowe, P.C.

(57) ABSTRACT

A rock true triaxial dynamic compression-shear test equipment, and method under deep complex structure conditions, includes a counterforce framework, a pressure chamber, a base platform and four actuators. A pressure chamber transfer track is arranged on the base platform, and a pressure chamber transfer slipway is arranged on the tracks. The pressure chamber is a split structure. A pressure chamber
(Continued)

base is located on the pressure chamber transfer slipway, and a pressure chamber barrel is provided with a pressure chamber barrel lift type bearing table and a pressure chamber barrel hoisting mechanism. The pressure chamber is provided with pressure chamber barrel and base packaging fixtures.

7 Claims, 7 Drawing Sheets

(51) Int. Cl.
  *G01N 33/24* (2006.01)
  *G01N 3/12* (2006.01)
  *G01N 3/36* (2006.01)
(58) Field of Classification Search
  CPC .. G01N 3/18; G01N 1/28; G01N 3/02; G01N 29/00; G01N 3/10; G01N 33/24; G01N 3/08; G01N 3/303; G01N 3/04; G01F 22/00; G11B 33/04
  See application file for complete search history.

(56) References Cited

U.S. PATENT DOCUMENTS

2018/0313727 A1* 11/2018 Feng .................. G01N 3/12
2018/0340874 A1* 11/2018 Liu ..................... G01N 3/12

FOREIGN PATENT DOCUMENTS

| CN | 205103090 U | 3/2016 |
| CN | 107014690 A | 8/2017 |
| CN | 107860663 A | 3/2018 |
| CN | 110031329 A | 7/2019 |
| CN | 112014227 A | 12/2020 |

* cited by examiner

ROCK TRUE TRIAXIAL DYNAMIC COMPRESSION-SHEAR TEST EQUIPMENT AND METHOD UNDER DEEP COMPLEX STRUCTURE CONDITIONS

BACKGROUND OF THE INVENTION

1. Field of the Invention

The present invention relates to a test equipment and method, and more particularly to a rock true triaxial dynamic compression-shear test equipment and method under deep complex structure conditions.

2. The Prior Arts

Deep shaft mining is the only way to obtain resources at present for deep metal underground mines. Deep shaft excavation passes through different strata from top to bottom, having the characteristics of large rock property changes, developed structural stress, multiple large fault structures and multiple discontinuous rock mass surfaces caused by local fracture. Besides, underground rock masses are subjected to a general stress state with $\sigma_1 > \sigma_2 > \sigma_3$ (where $\sigma_1$ is the maximum principal stress, $\sigma_2$ is the intermediate principal stress, and $\sigma_3$ is the minimum principal stress), which not only increases with overburden depth, but also changes significantly due to the influence of structural stress, so that the geological environment and rock mechanics conditions are extremely complex, and geological disasters such as sudden collapse, rock burst, large deformation, and blast-induced rock mass structural instability often occur. Therefore, it is necessary to deeply study the evolution characteristics of mechanical properties of rock mass fracture and brittle failure caused by dynamic compression, dynamic shear and quick unloading of deep rocks under true triaxial stress conditions.

At present, the true triaxial dynamics test in the rock mechanics framework is mainly divided into the following categories: (1) a flexible or rigid true triaxial test equipment is loaded to a certain high true triaxial stress level, a single surface is suddenly unloaded to form a free surface, and rock burst is simulated through inducing rock violent fracture processing; (2) a flexible or rigid true triaxial test equipment is loaded to a certain high true triaxial stress level, a single surface is suddenly unload to form a free surface, besides, actuators apply low-frequency disturbance load, and rock burst is simulated by stimulating rock violent fracture processing; (3) a true triaxial test equipment having a three-dimensional orthogonal Hopkinson bar structure is used to impact a rock specimen to simulate the dynamics failure of rocks; and (4) a high-pressure hard rock low-frequency disturbance and high-speed impact type true triaxial test equipment combined with a rigid true triaxial loading framework and a one-dimensional Hopkinson bar is used to simulate the failure of complete rocks under dynamic conditions. However, for engineering rock masses under complex deep structures and high ground stress conditions, if the dynamic compression and shear mechanical behaviors of complete rocks and rocks with respective discontinuous surfaces under true triaxial dynamic stress action need to be further studied, general true triaxial dynamics test equipments and methods for rock mechanics still have limitations. Therefore, it is imperative to develop a new set of rock true triaxial dynamic compression-shear test equipment and method under deep complex structure conditions.

SUMMARY OF THE INVENTION

In view of the shortcomings existing in the prior art, a primary objective of the present invention is to provide a rock true triaxial dynamic compression-shear test equipment and method under deep complex structure conditions. 5000-meter-level overburden depth ground stress conditions can be simulated, complete rock specimens subjected to different loading and unloading stress paths under high stress conditions and tests having types of discontinuous structure (jointing, bedding and crack) rock specimen fracture deformation, sudden instability, dynamic compression shear, low-cycle fatigue and the like can be executed, the test equipment and the method can be used to study a rock critical fracture and instability dynamics mechanism under different rock external rigidity and three-dimensional stress combined conditions, and the needs of deep engineering rock masses failure test research under the structural control of discontinuous surfaces and under dynamic action are effectively met.

To achieve the above objectives, the present invention provides a rock true triaxial dynamic compression-shear test equipment under deep complex structure conditions comprising a counterforce framework, a pressure chamber, a base platform, a first maximum principal stress actuator, a second maximum principal stress actuator, a first intermediate principal stress actuator and a second intermediate principal stress actuator.

Wherein the counterforce framework is fixedly arranged on a ground.

Wherein the first maximum principal stress actuator and the second maximum principal stress actuator are symmetrically arranged at an upper end and a lower end of the counterforce framework.

Wherein the first intermediate principal stress actuator and the second intermediate principal stress actuator are symmetrically arranged at a left end and a right end of the counterforce framework.

Wherein the base platform is fixedly arranged on the ground on a front side and a rear side of the counterforce framework.

Wherein a pressure chamber transfer track is horizontally paved at a top part of the base platform, is a parallel dual-track structure, and runs through a central working cavity of the counterforce framework.

Wherein a pressure chamber transfer slipway is arranged on the pressure chamber transfer track, and can move in a straight line along the pressure chamber transfer track.

Wherein the pressure chamber is a split barrel-shaped structure, is used to supply a minimum principal stress and comprises a pressure chamber base and a pressure chamber barrel, and the pressure chamber base and the pressure chamber barrel are buckled to form the pressure chamber.

Wherein the pressure chamber base is arranged on the pressure chamber transfer slipway, and the pressure chamber base can move together with the pressure chamber transfer slipway.

Wherein a pressure chamber barrel hoisting mechanism is arranged above the base platform, a pressure chamber barrel lift type bearing table is hidden and arranged in the base platform just below a suspension arm of the pressure chamber barrel hoisting mechanism, and a pressure chamber barrel and base packaging fixture is arranged on a left side and a right side of the pressure chamber barrel lift type bearing table.

In one embodiment, the counterforce framework is an annular plane integrated structure and has a polygonal section, a bottom plane of the counterforce framework is fixedly connected with the ground through a principal support base, and a side support base is arranged between the principal support base and a bottom slope of the counterforce framework; wherein the first maximum principal stress actuator is vertically hidden and embedded at the upper end of the counterforce framework, the second maximum principal stress actuator is vertically hidden and embedded at the lower end of the counterforce framework, and the first maximum principal stress actuator and the second maximum principal stress actuator are coaxially distributed; and wherein the first intermediate principal stress actuator is horizontally hidden and embedded at the left end of the counterforce framework, the second intermediate principal stress actuator is horizontally hidden and embedded at the right end of the counterforce framework, and the first intermediate principal stress actuator and the second intermediate principal stress actuator are coaxially distributed.

In one embodiment, each of the first maximum principal stress actuator, the second maximum principal stress actuator, the first intermediate principal stress actuator and the second intermediate principal stress actuator comprises a cylinder barrel, a piston rod, a cylinder tail cover plate and a cylinder head cover plate; wherein the cylinder tail cover plate is fixedly mounted at a tail end barrel opening of the cylinder barrel in a sealed manner, the cylinder head cover plate is fixedly mounted at a head end barrel opening of the cylinder barrel in a sealed manner, the cylinder barrel is coaxially sleeved on the piston rod, a rodless cavity in the cylinder barrel and the cylinder tail cover plate are on a same side, and a rod cavity in the cylinder barrel and the cylinder head cover plate are on a same side; wherein the piston rod penetrates through the cylinder head cover plate in a sealed manner, a static pressure support seal sleeve is sleeved between the piston rod of the rod cavity and the cylinder barrel, and a dustproof sleeve is arranged between the piston rod and a penetrating hole of the cylinder head cover plate; wherein a magnetostriction type displacement sensor is connected between the piston rod and the cylinder tail cover plate; wherein an overhanging end of the piston rod is connected to a spoke type load sensor, a load sensor adapter is arranged between the spoke type load sensor and the piston rod, and a pressure head is fixedly connected to an outer end of the spoke type load sensor; and wherein a side force resistant mechanism is arranged at a periphery of the load sensor adapter.

In one embodiment, a first self-balancing piston rod is vertically arranged in a center of a top part of the pressure chamber barrel, the first self-balancing piston rod and the pressure chamber barrel are sealed through a first flange end cover, one end of the first self-balancing piston rod extends outside the pressure chamber barrel, another end of the first self-balancing piston rod extends into the pressure chamber barrel, and a first linear variable differential transformer (LVDT) displacement sensor is connected between the first self-balancing piston rod and the pressure chamber barrel; wherein a second self-balancing piston rod is vertically arranged in a center of the pressure chamber base, the second self-balancing piston rod and the pressure chamber base are sealed through a second flange end cover, one end of the second self-balancing piston rod extends to a position below the pressure chamber base, another end of the second self-balancing piston rod extends to a position above the pressure chamber base, and a second linear variable differential transformer (LVDT) displacement sensor is connected between the second self-balancing piston rod and the pressure chamber base; wherein a third self-balancing piston rod is horizontally arranged on a left side part of the pressure chamber barrel, the third self-balancing piston rod and the pressure chamber barrel are sealed through a third flange end cover, one end of the third self-balancing piston rod extends outside the pressure chamber barrel, another end of the third self-balancing piston rod extends into the pressure chamber barrel, and a third linear variable differential transformer (LVDT) displacement sensor is connected between the third self-balancing piston rod and the pressure chamber barrel; wherein a fourth self-balancing piston rod is horizontally arranged on a right side part of the pressure chamber barrel, the fourth self-balancing piston rod and the pressure chamber barrel are sealed through a fourth flange end cover, one end of the fourth self-balancing piston rod extends outside the pressure chamber barrel, another end of the fourth self-balancing piston rod extends into the pressure chamber barrel, and a fourth linear variable differential transformer (LVDT) displacement sensor is connected between the fourth self-balancing piston rod and the pressure chamber barrel; wherein the first self-balancing piston rod and the second self-balancing piston rod are coaxially distributed, and the third self-balancing piston rod and the fourth self-balancing piston rod are coaxially distributed; and wherein hoisting lugs are arranged outside the pressure chamber barrel.

In one embodiment, a slipway guide sliding block is fixedly arranged on a lower surface of the pressure chamber transfer slipway, and is in sliding connection with the pressure chamber transfer track; wherein a rack is fixedly mounted on a side part of one track of the dual-track structure of the pressure chamber transfer track, and is parallel to the pressure chamber transfer track; wherein a hydraulic motor is vertically mounted on the pressure chamber transfer slipway, a power output shaft of the hydraulic motor faces and extends below the pressure chamber transfer slipway, a gear is fixedly mounted on the power output shaft of the hydraulic motor, and the gear and the rack are meshed.

In one embodiment, the pressure chamber barrel and base packaging fixture comprises a left half fixture and a right half fixture, each of the left half fixture and the right half fixture comprises a semi-ring jacket, a jacket guide supporting table, a jacket fixing guide rail, a jacket following guide rail, a jacket sliding block and a jacket electric pushing mechanism; wherein the jacket guide supporting table is fixedly arranged on one side of the base platform, the jacket fixing guide rail is horizontally and fixedly mounted on an upper surface of the jacket guide supporting table, and the jacket fixing guide rail is a parallel dual-rail structure; wherein the jacket following guide rail is horizontally and fixedly mounted on an upper surface of the pressure chamber transfer slipway, is a parallel dual-rail structure, and is completely the same as the jacket fixing guide rail in a layout height and a rail gauge; wherein the jacket sliding block is fixedly arranged on a lower surface of the semi-ring jacket, and the jacket sliding block is in sliding connection and cooperation with the jacket following guide rail and the jacket fixing guide rail; wherein the jacket electric pushing mechanism is arranged between the semi-ring jacket and the jacket guide supporting table, and the jacket electric pushing mechanism is used for driving the semi-ring jacket to move in a straight line on the jacket following guide rail and the jacket fixing guide rail; and wherein transverse pressure elbow clamps are respectively arranged on the semi-ring jacket of the left half fixture and the semi-ring jacket of the right half fixture, and the pressure chamber base and the pressure chamber barrel are packaged and fixed through the two semi-ring jackets which are buckled together.

To achieve the above objectives, the present invention provides a test method for the rock true triaxial dynamic compression-shear test equipment under deep complex structure conditions and comprises the following steps:

step I: preparing rock specimens, packaging the rock specimens with mutually-buckled pressure blocks, additionally preparing three sets of LVDT displacement sensors, combining the three sets of linear variable differential transformer (LVDT) displacement sensors with the rock specimens and the mutually-buckled pressure blocks together to finally form a specimen combination, and performing volume change measurement on the rock specimens through respectively using the three sets of LVDT displacement sensors in a large principal stress direction, an intermediate principal stress direction and a minimum principal stress direction;

step II: adjusting the test equipment to an initial state, wherein in the initial state, the pressure chamber base is located at a front station of the counterforce framework, the pressure chamber barrel is located on the pressure chamber barrel lift type bearing table at a rear station of the counterforce framework, and a semi-ring jacket of a left half fixture of the pressure chamber barrel and base packaging fixture and a semi-ring jacket of a right half fixture of the pressure chamber barrel and base packaging fixture are in a separated state;

step III: placing the prepared specimen combination at a top end of a second self-balancing piston rod of the pressure chamber base, and adjusting positions of the three sets of LVDT displacement sensors and an extension quantity of a contact probe on the specimen combination to enable the three sets of LVDT displacement sensors to be within a test measurement range;

step IV: firstly, vertically hoisting the pressure chamber barrel from the pressure chamber barrel lift type bearing table through the pressure chamber barrel hoisting mechanism, then controlling the pressure chamber barrel lift type bearing table to fall down to a lower position, then starting a hydraulic motor, and under a meshing transmission action of a gear and a rack, and enabling the pressure chamber transfer slipway bearing the pressure chamber base and the specimen combination to move along the pressure chamber transfer track until the pressure chamber base moves just below the pressure chamber barrel, so that at the time, a jacket fixing guide rail on a jacket guide supporting table and a corresponding jacket following guide rail on the pressure chamber transfer slipway are accurately linked together;

step V: enabling the pressure chamber barrel to fall down onto the pressure chamber base through the pressure chamber barrel hoisting mechanism so that the pressure chamber barrel and the pressure chamber base are buckled together, and at this time, the specimen combination is located inside the pressure chamber barrel, then enabling the suspension arm of the pressure chamber barrel hoisting mechanism and hoisting lugs outside the pressure chamber barrel to be disconnected, and then controlling the suspension arm of the pressure chamber barrel hoisting mechanism to elevate to reset;

step VI: starting a jacket electric pushing mechanism to enable the semi-ring jacket to move, enabling a jacket sliding block at a bottom part of the semi-ring jacket to move to the jacket following guide rail from the jacket fixing guide rail until the semi-ring jacket of the left half fixture and the semi-ring jacket of the right half fixture are completely buckled together, then locking the two semi-ring jackets into a whole through transverse pressure elbow clamps, and then controlling the jacket electric pushing mechanism to reset;

step VII: starting the hydraulic motor again, enabling the pressure chamber transfer slipway bearing the pressure chamber and the specimen combination to move to a test station where the counterforce framework is located, and then pre-clamping the specimen combination in the pressure chamber through cooperation of the first self-balancing piston rod, the second self-balancing piston rod, the third self-balancing piston rod and the fourth self-balancing piston rod on the pressure chamber;

step VIII: firstly filling hydraulic oil into the pressure chamber until minimum principal stress hydraulic pressure loading is completed, then starting the first maximum principal stress actuator, the second maximum principal stress actuator, the first intermediate principal stress actuator and the second intermediate principal stress actuator to apply maximum principal stress and intermediate principal stress to the rock specimens in the specimen combination, then performing a rock true triaxial dynamic compression-shear test, and besides, recording test data;

step IX: after the test is completed, firstly controlling the first maximum principal stress actuator, the second maximum principal stress actuator, the first intermediate principal stress actuator and the second intermediate principal stress actuator to reset, then unloading the minimum principal stress hydraulic pressure and completing hydraulic oil discharge;

step X: starting the hydraulic motor, enabling the pressure chamber transfer slipway bearing the pressure chamber and the specimen combination to move to the rear station of the counterforce framework, firstly releasing locking of the two semi-ring jackets by the transverse pressure elbow clamps, and then controlling the two semi-ring jackets to return to the respective initial positions by the jacket electric pushing mechanisms to complete separation of the two semi-ring jackets;

step XI: controlling the suspension arm of the pressure chamber barrel hoisting mechanism to fall, enabling the hoisting lugs outside the pressure chamber barrel and the suspension arm of pressure chamber barrel hoisting mechanism to be connected together, then controlling the suspension arm of the pressure chamber barrel hoisting mechanism to rise to enable the pressure chamber barrel to rise to a high position, at this time, enabling the pressure chamber barrel and the pressure chamber base to complete separation, and besides, removing the exposed specimen combination from the top end of the second self-balancing piston rod of the pressure chamber base; and step XII: starting the hydraulic motor again, enabling the pressure chamber transfer slipway bearing the pressure chamber base to move to the front station of the counterforce framework, besides, controlling the pressure chamber barrel lift type bearing table at the rear station of the counterforce framework to rise, and finally, enabling the pressure chamber barrel to drop onto the pressure chamber barrel lift type bearing table through the pressure chamber barrel hoisting mechanism.

The rock true triaxial dynamic compression-shear test equipment and method under deep complex structure conditions disclosed by the present invention have beneficial effects:

5000-meter-level overburden depth ground stress conditions can be simulated, complete rock specimens of different loading and unloading stress paths under high stress conditions and tests having types of discontinuous structure (jointing, bedding and crack) rock specimen fracture deformation, sudden instability, dynamic compression shear, low-cycle fatigue and the like can be executed, the test equipment and the method can be used to study a rock critical fracture and instability dynamics mechanism under different rock external rigidity and three-dimensional stress combined conditions, and the needs of deep engineering rock masses failure test research under the structural control of discontinuous surfaces and under dynamic action are effectively met.

DETAILED DESCRIPTION OF THE PREFERRED EMBODIMENT

Figure 1:
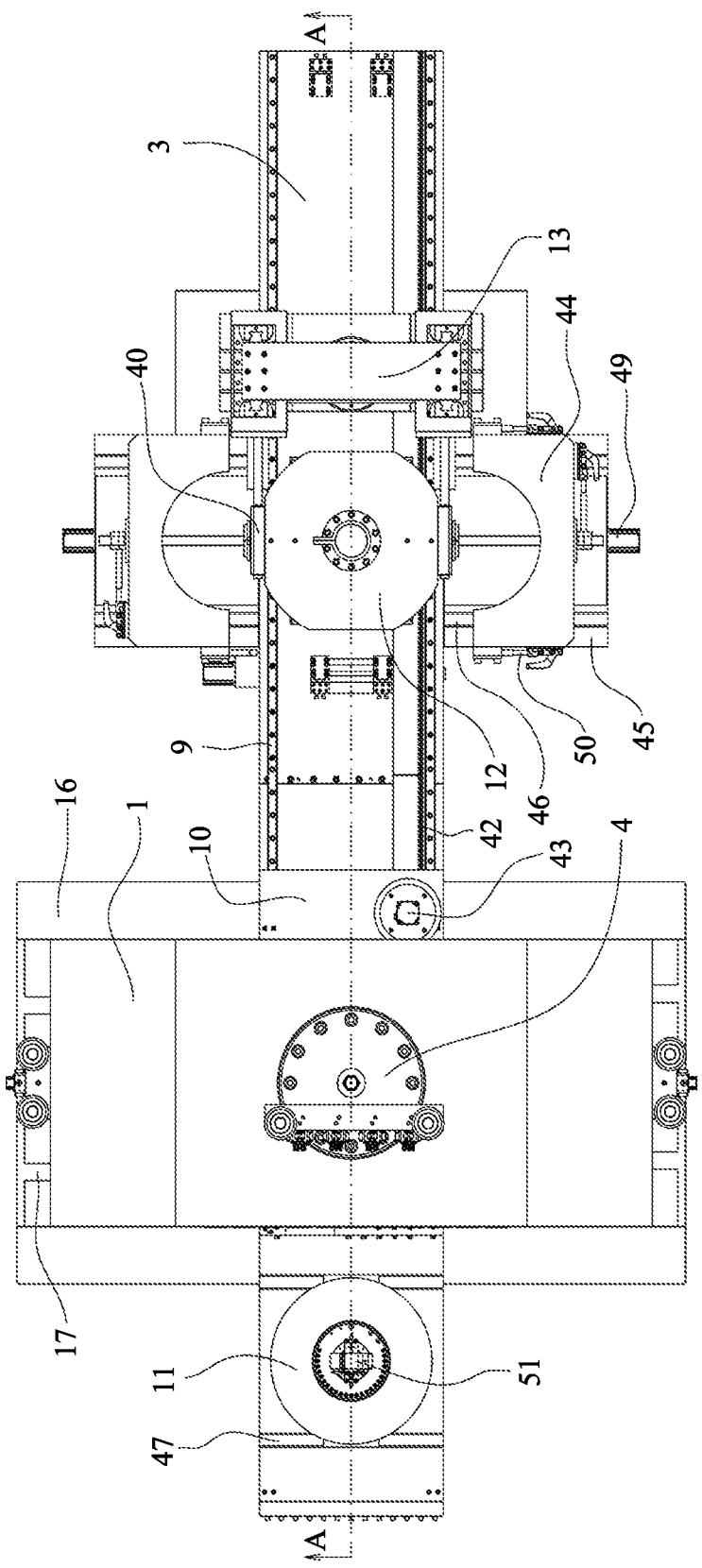
FIG. 1 shows a top view of a rock true triaxial dynamic compression-shear test equipment under deep complex structure conditions according to present invention the invention, wherein the test equipment is in an initial state.

The present invention will be further described in detail below with reference to the drawings and specific embodiments.

As shown in FIG. 1-FIG. 7, the present invention is to provide a rock true triaxial dynamic compression-shear test equipment under deep complex structure conditions comprising a counterforce framework 1, a pressure chamber 2, a base platform 3, a first maximum principal stress actuator 4, a second maximum principal stress actuator 5, a first intermediate principal stress actuator 6 and a second intermediate principal stress actuator 7. The counterforce framework 1 is fixedly arranged on a ground 8. The first maximum principal stress actuator 4 and the second maximum principal stress actuator 5 are symmetrically arranged at an upper end and a lower end of the counterforce framework 1. The first intermediate principal stress actuator 6 and the second intermediate principal stress actuator 7 are symmetrically arranged at a left end and a right end of the counterforce framework 1. The base platform 3 is fixedly arranged on the ground on a front side and a rear side of the counterforce framework 1. A pressure chamber transfer track 9 is horizontally paved at a top part of the base platform 3, is a parallel dual-track structure, and runs through a central working cavity of the counterforce framework 1. A pressure chamber transfer slipway 10 is arranged on the pressure chamber transfer track 9, and can move in a straight line along the pressure chamber transfer track 9. The pressure chamber 2 is a split barrel-shaped structure, is used to supply a minimum principal stress and comprises a pressure chamber base 11 and a pressure chamber barrel 12, and the pressure chamber base 11 and the pressure chamber barrel 12 are buckled to form the pressure chamber 2. The pressure chamber base 11 is arranged on the pressure chamber transfer slipway 10, and the pressure chamber base 11 can move together with the pressure chamber transfer slipway 10. A pressure chamber barrel hoisting mechanism 13 is arranged above the base platform 3, a pressure chamber barrel lift type bearing table 14 is hidden and arranged in the base platform 3 just below a suspension arm of the pressure chamber barrel hoisting mechanism 13, and a pressure chamber barrel and base packaging fixture 15 is arranged on a left side and a right side of the pressure chamber barrel lift type bearing table 14.

As shown in FIG. 1 to FIG. 4, the counterforce framework 1 is an annular plane integrated structure and has a polygonal section, a bottom plane of the counterforce framework 1 is fixedly connected with the ground 8 through a principal support base 16, and a side support base 17 is arranged between the principal support base 16 and a bottom slope of the counterforce framework 1. The first maximum principal stress actuator 4 is vertically hidden and embedded at the upper end of the counterforce framework 1, the second maximum principal stress actuator 5 is vertically hidden and embedded at the lower end of the counterforce framework 1, and the first maximum principal stress actuator 4 and the second maximum principal stress actuator 5 are coaxially distributed. The first intermediate principal stress actuator 6 is horizontally hidden and embedded at the left end of the counterforce framework 1, the second intermediate principal stress actuator 7 is horizontally hidden and embedded at the right end of the counterforce framework 1, and the first intermediate principal stress actuator 6 and the second intermediate principal stress actuator 7 are coaxially distributed.

In this embodiment, the counterforce framework 1 needs to meet the design requirements of an ultra-high rigidity plane loading counterforce framework. For this reason, the counterforce framework 1 is made of 42CrMo materials with a forging process, the yield strength of the counterforce framework 1 can reach 930 MPa, and the overall effective rigidity of the counterforce framework 1 can reach 20 GN/m or above.

Figure 5:
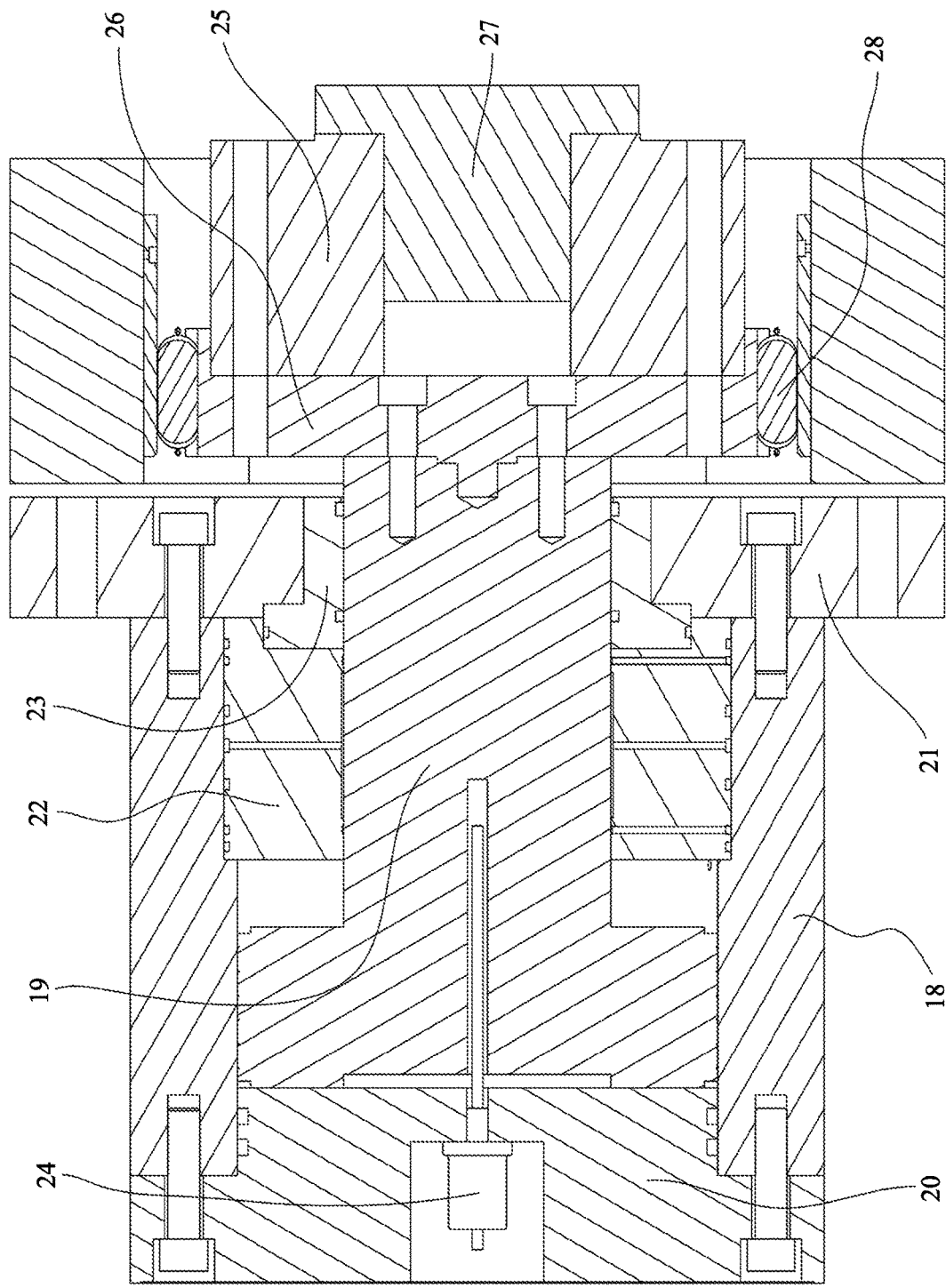
FIG. 5 shows a cross-sectional view of each actuator according to the present invention.

As shown in FIG. 5, each of the first maximum principal stress actuator 4, the second maximum principal stress actuator 5, the first intermediate principal stress actuator 6 and the second intermediate principal stress actuator 7 comprises a cylinder barrel 18, a piston rod 19, a cylinder tail cover plate 20 and a cylinder head cover plate 21. The cylinder tail cover plate 20 is fixedly mounted at a tail end barrel opening of the cylinder barrel 18 in a sealed manner, the cylinder head cover plate 21 is fixedly mounted at a head end barrel opening of the cylinder barrel 18 in a sealed manner, the cylinder barrel 18 is coaxially sleeved on the piston rod 19, a rodless cavity in the cylinder barrel 18 and the cylinder tail cover plate 20 are on a same side, and a rod cavity in the cylinder barrel 18 and the cylinder head cover plate 21 are on a same side. The piston rod 19 penetrates through the cylinder head cover plate 21 in a sealed manner, a static pressure support seal sleeve 22 is sleeved between the piston rod 19 of the rod cavity and the cylinder barrel 18, and a dustproof sleeve 23 is arranged between the piston rod 19 and a penetrating hole of the cylinder head cover plate 21. A magnetostriction type displacement sensor 24 is connected between the piston rod 19 and the cylinder tail cover plate 20. An overhanging end of the piston rod 19 is connected to a spoke type load sensor 25, a load sensor adapter 26 is arranged between the spoke type load sensor 25 and the piston rod 19, and a pressure head 27 is fixedly connected to an outer end of the spoke type load sensor 25. A side force resistant mechanism 28 is arranged at a periphery of the load sensor adapter 26.

In this embodiment, the first maximum principal stress actuator 4, the second maximum principal stress actuator 5, the first intermediate principal stress actuator 6 and the second intermediate principal stress actuator 7 all need to achieve design requirements of large-tonnage low-friction dynamic servo actuators. For this reason, each actuator is provided with one static pressure support seal sleeve 22, so that the characteristics of small starting frequency, ultrahigh kinematic accuracy, high control accuracy and good accuracy retentivity are guaranteed. Each actuator is provided with one magnetostriction type displacement sensor 24 and one spoke type load sensor 25, a loading position of the piston rod 19 is monitored through the magnetostriction type displacement sensor 24, and a loading load of the actuators is monitored through the spoke type load sensor 25. Each actuator is also provided with one side force resistant mechanism 28, side force generated during piston loading is eliminated through the side force resistant mechanisms 28, so that the influence of the side force on test data can be eliminated.

Figure 6:
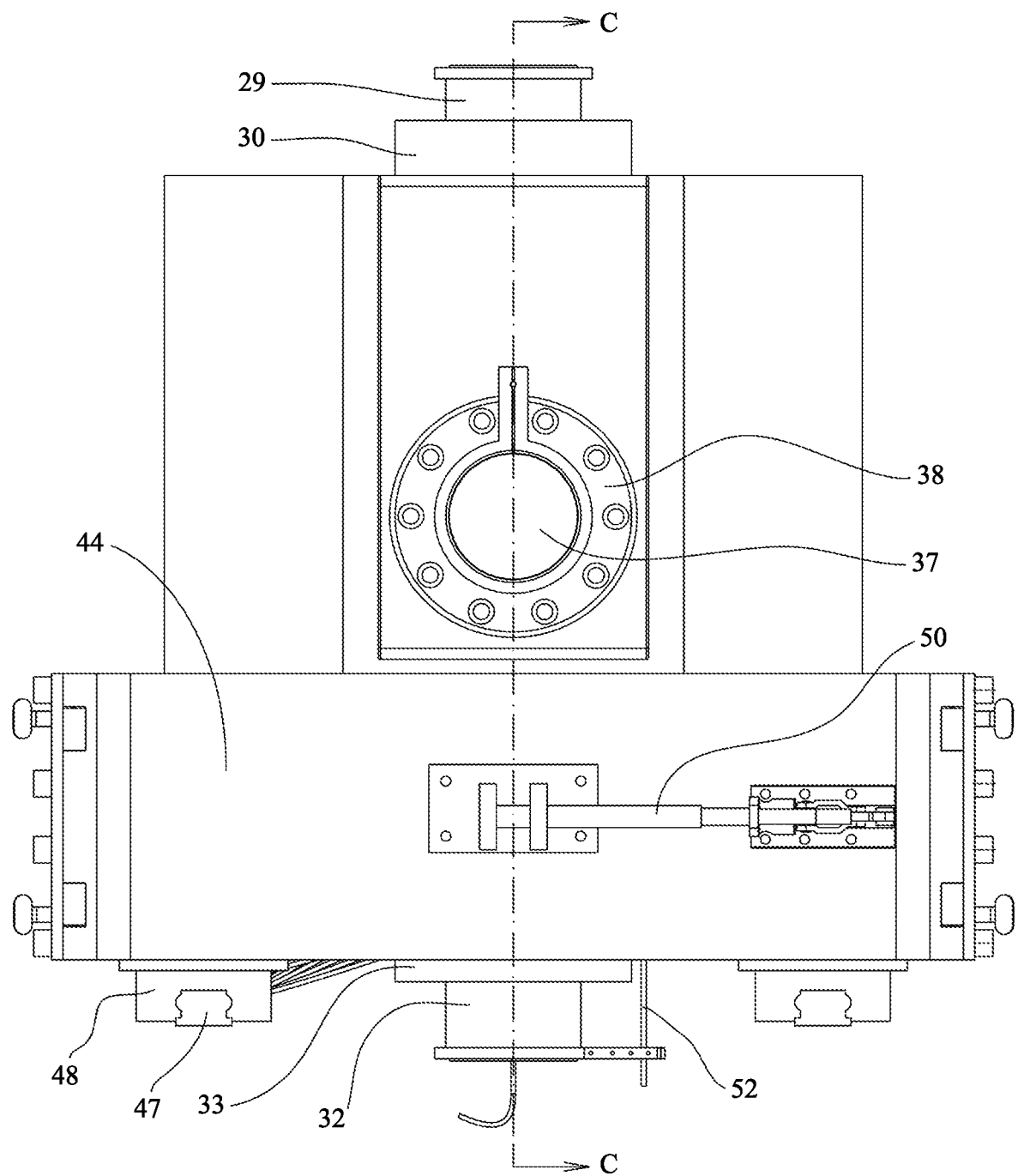
FIG. 6 shows a schematic structural view of the pressure chamber according to the present invention.
Figure 7:
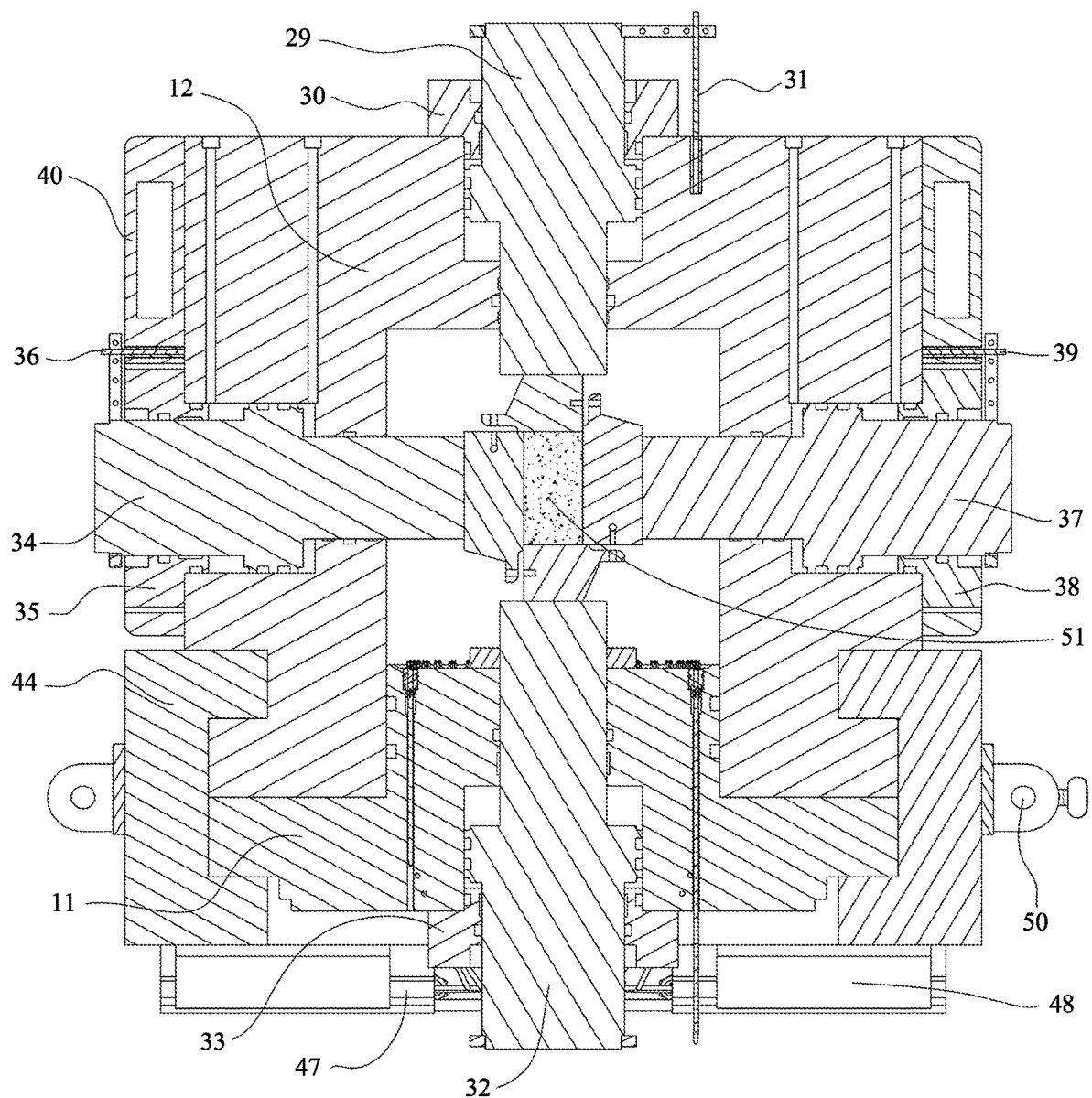
FIG. 7 shows a C-C cross-sectional view in FIG. 6.

As shown in FIG. 6 and FIG. 7, a first self-balancing piston rod 29 is vertically arranged in a center of a top part of the pressure chamber barrel 12, the first self-balancing piston rod 29 and the pressure chamber barrel 12 are sealed through a first flange end cover 30, one end of the first self-balancing piston rod 29 extends outside the pressure chamber barrel 12, another end of the first self-balancing piston rod 29 extends into the pressure chamber barrel 12, and a first linear variable differential transformer (LVDT) displacement sensor 31 is connected between the first self-balancing piston rod 29 and the pressure chamber barrel 12. A second self-balancing piston rod 32 is vertically arranged in a center of the pressure chamber base 11, the second self-balancing piston rod 32 and the pressure chamber base 11 are sealed through a second flange end cover 33, one end of the second self-balancing piston rod 32 extends to a position below the pressure chamber base 11, another end of the second self-balancing piston rod 32 extends to a position above the pressure chamber base 11, and a second linear variable differential transformer (LVDT) displacement sensor 52 is connected between the second self-balancing piston rod 32 and the pressure chamber base 11. A third self-balancing piston rod 34 is horizontally arranged on a left side part of the pressure chamber barrel 12, the third self-balancing piston rod 34 and the pressure chamber barrel 12 are sealed through a third flange end cover 35, one end of the third self-balancing piston rod 34 extends outside the pressure chamber barrel 12, another end of the third self-balancing piston rod 34 extends into the pressure chamber barrel 12, and a third linear variable differential transformer (LVDT) displacement sensor 36 is connected between the third self-balancing piston rod 34 and the pressure chamber barrel 12. A fourth self-balancing piston rod 37 is horizontally arranged on a right side part of the pressure chamber barrel 12, the fourth self-balancing piston rod 37 and the pressure chamber barrel 12 are sealed through a fourth flange end cover 38, one end of the fourth self-balancing piston rod 37 extends outside the pressure chamber barrel 12, another end of the fourth self-balancing piston rod 37 extends into the pressure chamber barrel 12, and a fourth linear variable differential transformer (LVDT) displacement sensor 39 is connected between the fourth self-balancing piston rod 37 and the pressure chamber barrel 12. The first self-balancing piston rod 29 and the second self-balancing piston rod 32 are coaxially distributed, and the third self-balancing piston rod 34 and the fourth self-balancing piston rod 37 are coaxially distributed. Hoisting lugs 40 are arranged outside the pressure chamber barrel 12.

In this embodiment, the pressure chamber base 11 and the pressure chamber barrel 12 are made of 42CrMo materials with the forging process, and the yield strength can reach 930 MPa. After the pressure chamber base 11 and the pressure chamber barrel 12 are buckled to form the pressure chamber 2, the pressure chamber 2 can withstand a pressure of 120 MPa. Split design is used, so that a traditional specimen mounting hole is omitted, and the operating space of the specimens is increased. Through fine adjustment cooperation of the first self-balancing piston rod 29, the second self-balancing piston rod 32, the third self-balancing piston rod 34 and the fourth self-balancing piston rod 37, the specimens can be subjected to pre-positioning treatment.

Figure 2:
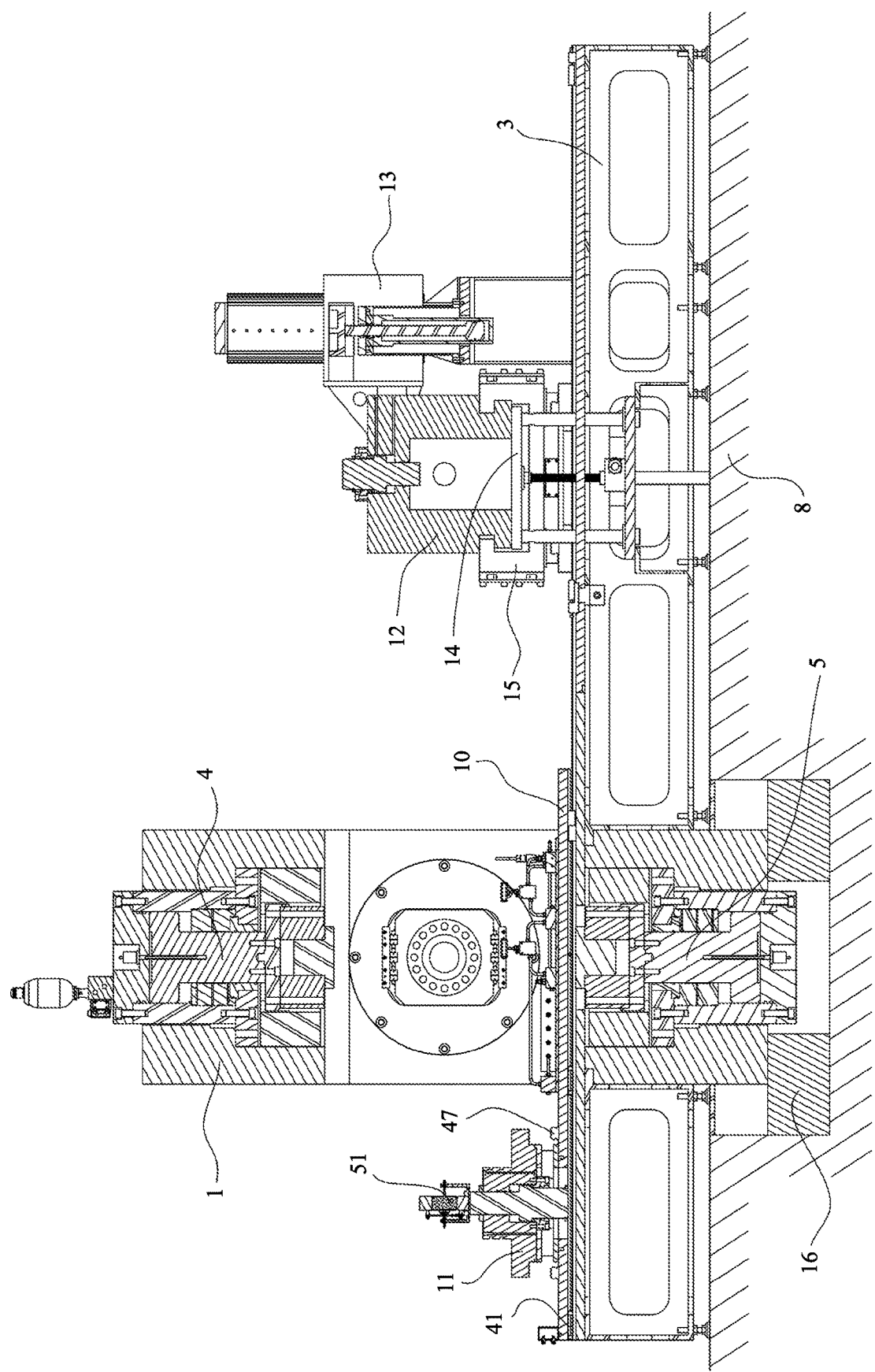
FIG. 2 shows an A-A cross-sectional view in FIG. 1.
Figure 3:
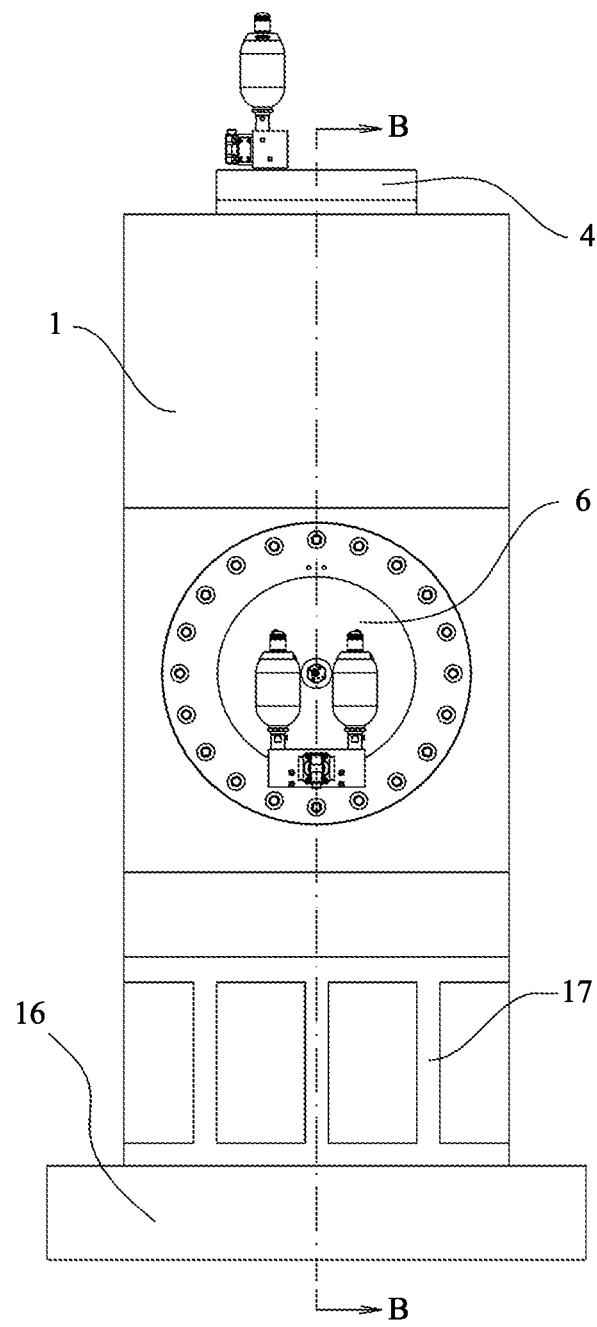
FIG. 3 shows a side view of a counterforce framework according to the present invention, wherein the counterforce framework is equipped with the actuators and in working state.
Figure 4:
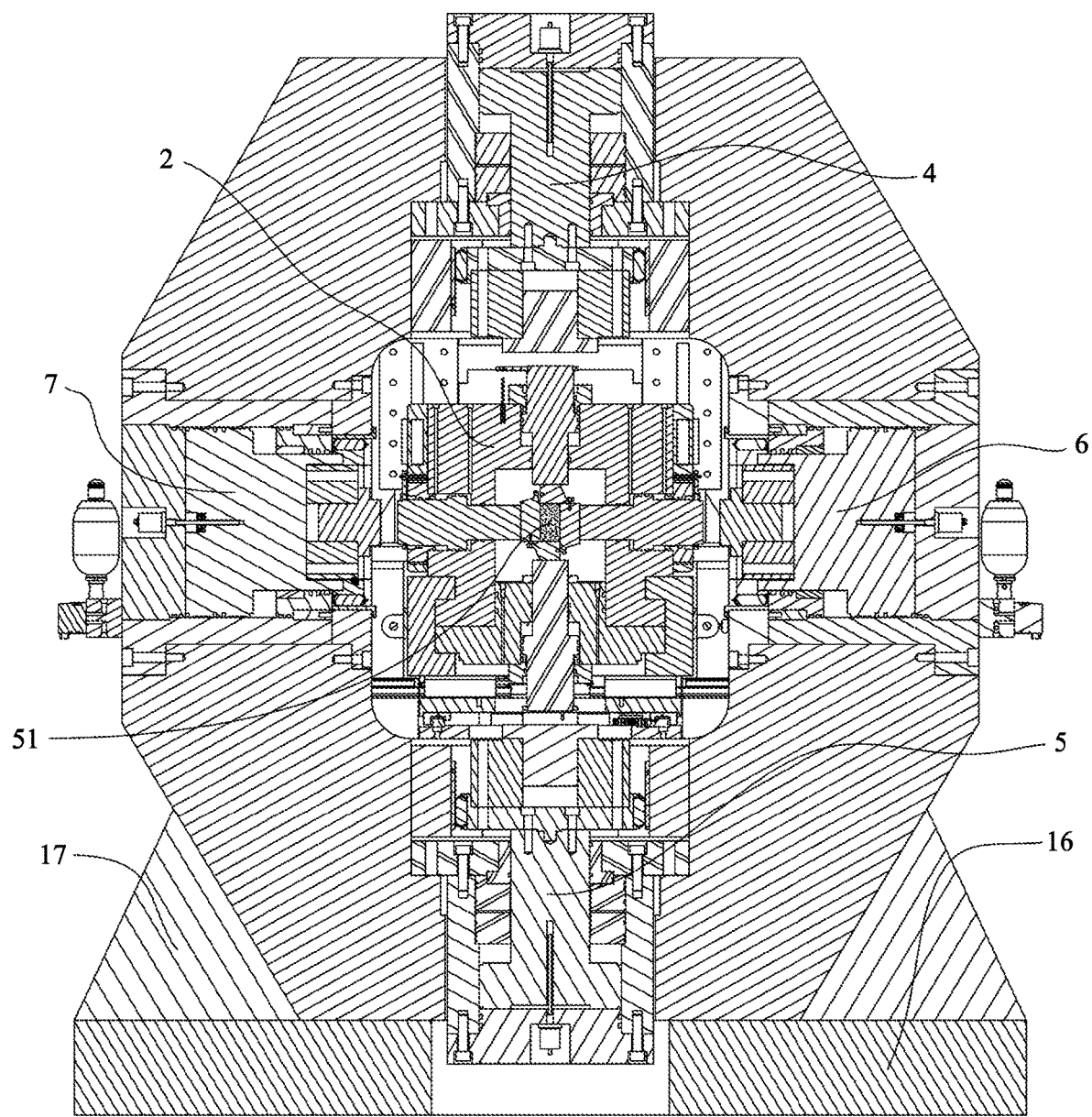
FIG. 4 shows a B-B cross-sectional view in FIG. 3.

As shown in FIG. 1 and FIG. 2, a slipway guide sliding block 41 is fixedly arranged on a lower surface of the pressure chamber transfer slipway 10, and is in sliding connection with the pressure chamber transfer track 9. A rack 42 is fixedly mounted on a side part of one track of the dual-track structure of the pressure chamber transfer track 9, and is parallel to the pressure chamber transfer track 9. A hydraulic motor 43 is vertically mounted on the pressure chamber transfer slipway 10, a power output shaft (not shown) of the hydraulic motor 43 faces and extends below the pressure chamber transfer slipway 10, a gear (not shown) is fixedly mounted on the power output shaft of the hydraulic motor 43, and the gear and the rack 42 are meshed.

As shown in FIG. 1 and FIG. 2 and FIG. 7, the pressure chamber barrel and base packaging fixture 15 comprises a left half fixture and a right half fixture each of the left half fixture and the right half fixture comprises a semi-ring jacket 44, a jacket guide supporting table 45, a jacket fixing guide rail 46, a jacket following guide rail 47, a jacket sliding block 48 and a jacket electric pushing mechanism 49. The jacket guide supporting table 45 is fixedly arranged in one side of the base platform 3, the jacket fixing guide rail 46 is horizontally and fixedly mounted on an upper surface of the jacket guide supporting table 45, and the jacket fixing guide rail 46 is a parallel dual-rail structure. The jacket following guide rail 47 is horizontally and fixedly mounted on an upper surface of the pressure chamber transfer slipway 10, is a parallel dual-rail structure, and is completely the same as the jacket fixing guide rail 46 in a layout height and a rail gauge. The jacket sliding block 48 is fixedly arranged on a lower surface of the semi-ring jacket 44, and the jacket sliding block 48 is in sliding connection and cooperation with the jacket following guide rail 47 and the jacket fixing guide rail 46. The jacket electric pushing mechanism 49 is arranged between the semi-ring jacket 44 and the jacket guide supporting table 45, and the jacket electric pushing mechanism 49 is used for driving the semi-ring jacket 44 to move in a straight line on the jacket following guide rail 47 and the jacket fixing guide rail 46. Transverse pressure elbow clamps 50 are respectively arranged on the semi-ring jacket 44 of the left half fixture and the semi-ring jacket 44 of the right half fixture, and the pressure chamber base 11 and the pressure chamber barrel 12 are packaged and fixed through the two semi-ring jackets 44 which are buckled together.

In the embodiment, a large-flow hydraulic oil source of the test equipment is designed in accordance with the concept of being energy-saving, demountable and recyclable. Five sets of oil pump combinations with different flows can be used to meet the requirements for large and small flows under different functions so as to achieve the purposes of saving energy, reducing heat generation and improving system stability. Combinations of servo valves with different flows are used to meet the requirements for the flows under different functional test conditions. In addition, in order to meet different test requirements for static, dynamic, stress-strain overall-process curves and the like, 4 sets of 100 L/min oil pumps can be used in parallel, and can be turned on individually or at the same time, so that the large flow required for dynamic control and the small flow required for overall-process curves can be realized, excessive flow losses are avoided, saving of electric energy is realized, besides, heat generation of the equipment is avoided, and the reliability and the stability of the equipment are improved. In order to ensure the progress of the test, an EDC i70 controller produced in Germany can be used as a main control element. The EDC i70 is a multi-channel application and a built-in case, three principal stress control commands and data acquisition functions can be completed on a common software platform.

The present invention is to provide a test method for the rock true triaxial dynamic compression-shear test equipment under deep complex structure conditions and comprises the following steps:

step I: preparing rock specimens, packaging the rock specimens with mutually-buckled pressure blocks, additionally preparing three sets of linear variable differential transformer (LVDT) displacement sensors (not shown), combining the three sets of LVDT displacement sensors with the rock specimens and the mutually-buckled pressure blocks together to finally form a specimen combination 51, and performing volume change measurement on the rock specimens through respectively using the three sets of LVDT displacement sensors in a large principal stress direction, an intermediate principal stress direction and a minimum principal stress direction;

step II: adjusting the test equipment to an initial state, wherein in the initial state, the pressure chamber base 11 is located at a front station of the counterforce framework 1, the pressure chamber barrel 12 is located on the pressure chamber barrel lift type bearing table 14 at a rear station of the counterforce framework 1, and the semi-ring jacket 44 of the left half fixture of the pressure chamber barrel and base packaging fixture 15 and the semi-ring jacket 44 of the right half fixture of the pressure chamber barrel and base packaging fixture 15 are in a separated state;

step III: placing the prepared specimen combination 51 at a top end of the second self-balancing piston rod 32 of the pressure chamber base 11, and adjusting positions of the three sets of LVDT displacement sensors and an extension quantity of a contact probe (not shown) on the specimen combination 51 to enable the three sets of LVDT displacement sensors to be within a test measurement range;

step IV: firstly vertically hoisting the pressure chamber barrel 12 from the pressure chamber barrel lift type bearing table 14 through the pressure chamber barrel hoisting mechanism 13, then controlling the pressure chamber barrel lift type bearing table 14 to fall down to a lower position, then starting the hydraulic motor 43, and under the meshing transmission action of the gear and the rack 42, enabling the pressure chamber transfer slipway 10 bearing the pressure chamber base 11 and the specimen combination 51 to move along the pressure chamber transfer track 9 until the pressure chamber base 11 moves just below the pressure chamber barrel 12, so that at the time, a jacket fixing guide rail 46 on the jacket guide supporting table 45 and the jacket following guide rail 47 on the pressure chamber transfer slipway 10 are accurately linked together;

step V: enabling the pressure chamber barrel 12 to fall down onto the pressure chamber base 11 through the pressure chamber barrel hoisting mechanism 13 so that the pressure chamber barrel 12 and the pressure chamber base 11 are buckled together, and at this time, the specimen combination 51 is located inside the pressure chamber barrel 12, and then enabling the suspension arm of the pressure chamber barrel hoisting mechanism 13 and the hoisting lugs 40 outside the pressure chamber barrel 12 to be disconnected, and then controlling the suspension arm of the pressure chamber barrel hoisting mechanism 13 to elevate to reset;

step VI: starting a jacket electric pushing mechanism 49 to enable the semi-ring jacket 44 to move, enabling a jacket sliding block 48 at a bottom part of the semi-ring jacket 44 to move to the jacket following guide rail 47 from the jacket fixing guide rail 46 until the semi-ring jacket 44 of the left half fixture and the semi-ring jacket 44 of the right half fixture are completely buckled together, then locking the two semi-ring jackets 44 into a whole through the transverse pressure elbow clamps 50, and then controlling the jacket electric pushing mechanism 49 to reset;

step VII: starting the hydraulic motor 43 again, enabling the pressure chamber transfer slipway 10 bearing the pressure chamber 2 and the specimen combination 51 to move to a test station where the counterforce framework 1 is located, and then pre-clamping the specimen combination 51 in the pressure chamber 2 through the cooperation of the first self-balancing piston rod 29, the second self-balancing piston rod 32, the third self-balancing piston rod 34 and the fourth self-balancing piston rod 37 on the pressure chamber 2;

step VIII: firstly filling hydraulic oil into the pressure chamber 2 until minimum principal stress hydraulic pressure loading is completed, then starting the first maximum principal stress actuator 4, the second maximum principal stress actuator 5, the first intermediate principal stress actuator 6 and the second intermediate principal stress actuator 7 to apply maximum principal stress and intermediate principal stress to the rock specimens in the specimen combination 51, then performing a rock true triaxial dynamic compression-shear test, and besides, recording test data;

step IX: after the test is completed, firstly controlling the first maximum principal stress actuator 4, the second maximum principal stress actuator 5, the first intermediate principal stress actuator 6 and the second intermediate principal stress actuator 7 to reset, then unloading the minimum principal stress hydraulic pressure and completing hydraulic oil discharge;

step X: starting the hydraulic motor 43, enabling the pressure chamber transfer slipway 10 bearing the pressure chamber 2 and the specimen combination 51 to move to the rear station of the counterforce framework 1, firstly releasing the locking of the two semi-ring jackets 44 by the transverse pressure elbow clamps 50, and then controlling the two semi-ring jackets 44 to return to the respective initial positions by the jacket electric pushing mechanisms 49 to complete the separation of the two semi-ring jackets 44;

step XI: controlling the suspension arm of the pressure chamber barrel hoisting mechanism 13 to fall, enabling the hoisting lugs 40 outside the pressure chamber barrel 12 and the suspension arm of pressure chamber barrel hoisting mechanism 13 to be connected together, then controlling the suspension arm of the pressure chamber barrel hoisting mechanism 13 to rise to enable the pressure chamber barrel 12 to rise to a high position, at this time, enabling the pressure chamber barrel 12 and the pressure chamber base 11 to complete separation, and besides, removing the exposed specimen combination 51 from the top end of the second self-balancing piston rod 32 of the pressure chamber base 11; and step XII: starting the hydraulic motor 43 again, enabling the pressure chamber transfer slipway 10 bearing the pressure chamber base 11 to move to the front station of the counterforce framework 1, besides, controlling the pressure chamber barrel lift type bearing table 14 at the rear station of the counterforce framework 1 to rise, and finally enabling the pressure chamber barrel 12 to drop onto the pressure chamber barrel lift type bearing table 14 through the pressure chamber barrel hoisting mechanism 13.

The solutions in the embodiments are not intended to limit the scope of patent protection of the present invention. Any equivalent implementation or modification that does not deviate from the present invention is included in the patent scope of this case.

What is claimed is:

1. A rock true triaxial dynamic compression-shear test equipment under deep complex structure conditions, comprising:
    a counterforce framework;
    a pressure chamber;
    a base platform;
    a first maximum principal stress actuator;
    a second maximum principal stress actuator;
    a first intermediate principal stress actuator; and
    a second intermediate principal stress actuator;
    wherein the counterforce framework is fixedly arranged on a ground;
    wherein the first maximum principal stress actuator and the second maximum principal stress actuator are symmetrically arranged at an upper end and a lower end of the counterforce framework;
    wherein the first intermediate principal stress actuator and the second intermediate principal stress actuator are symmetrically arranged at a left end and a right end of the counterforce framework;
    wherein the base platform is fixedly arranged on the ground on a front side and a rear side of the counterforce framework;
    wherein a pressure chamber transfer track is horizontally paved at a top part of the base platform, is a parallel dual-track structure, and runs through a central working cavity of the counterforce framework;
    wherein a pressure chamber transfer slipway is arranged on the pressure chamber transfer track, and can move in a straight line along the pressure chamber transfer track;
    wherein the pressure chamber is a split barrel-shaped structure, is used to supply a minimum principal and comprises a pressure chamber base and a pressure chamber barrel, and the pressure chamber base and the pressure chamber barrel are buckled to form the pressure chamber;
    wherein the pressure chamber base is arranged on the pressure chamber transfer slipway, and the pressure chamber base can move together with the pressure chamber transfer slipway; and
    wherein a pressure chamber barrel hoisting mechanism is arranged above the base platform, a pressure chamber barrel lift type bearing table is hidden and arranged in the base platform just below a suspension arm of the pressure chamber barrel hoisting mechanism, and a pressure chamber barrel and base packaging fixture is arranged on a left side and a right side of the pressure chamber barrel lift type bearing table.

2. The test equipment according to claim 1, wherein the counterforce framework is an annular plane integrated structure and has a polygonal section, a bottom plane of the counterforce framework is fixedly connected with the ground through a principal support base, and a side support base is arranged between the principal support base and a bottom slope of the counterforce framework; wherein the first maximum principal stress actuator is vertically hidden and embedded at the upper end of the counterforce framework, the second maximum principal stress actuator is vertically hidden and embedded at the lower end of the counterforce framework, and the first maximum principal stress actuator and the second maximum principal stress actuator are coaxially distributed; and wherein the first intermediate principal stress actuator is horizontally hidden and embedded at the left end of the counterforce framework, the second intermediate principal stress actuator is horizontally hidden and embedded at the right end of the counterforce framework and the first intermediate principal stress actuator and the second intermediate principal stress actuator are coaxially distributed.

3. The test equipment according to claim 1, wherein each of the first maximum principal stress actuator, the second maximum principal stress actuator, the first intermediate principal stress actuator and the second intermediate principal stress actuator comprises a cylinder barrel, a piston rod, a cylinder tail cover plate and a cylinder head cover plate; wherein the cylinder tail cover plate is fixedly mounted at a tail end barrel opening of the cylinder barrel in a sealed manner, the cylinder head cover plate is fixedly mounted at a head end barrel opening of the cylinder barrel in a sealed manner, the cylinder barrel is coaxially sleeved on the piston rod, a rodless cavity in the cylinder barrel and the cylinder tail cover plate are on a same side, and a rod cavity in the cylinder barrel and the cylinder head cover plate are on a same side; wherein the piston rod penetrates through the cylinder head cover plate in a sealed manner, a static pressure support seal sleeve is sleeved between the piston rod of the rod cavity and the cylinder barrel, and a dustproof sleeve is arranged between the piston rod and a penetrating hole of the cylinder head cover plate; wherein a magnetostriction type displacement sensor is connected between the piston rod and the cylinder tail cover plate; wherein an overhanging end of the piston rod is connected to a spoke type load sensor, a load sensor adapter is arranged between the spoke type load sensor and the piston rod, and a pressure head is fixedly connected to an outer end of the spoke type load sensor; and wherein a side force resistant mechanism is arranged at a periphery of the load sensor adapter.

4. The test equipment according to claim 1, wherein a first self-balancing piston rod is vertically arranged in a center of a top part of the pressure chamber barrel, the first self-balancing piston rod and the pressure chamber barrel are sealed through a first flange end cover, one end of the first self-balancing piston rod extends outside the pressure chamber barrel, another end of the first self-balancing piston rod extends into the pressure chamber barrel, and a first linear variable differential transformer (LVDT) displacement sensor is connected between the first self-balancing piston rod and the pressure chamber barrel; wherein a second self-balancing piston rod is vertically arranged in a center of the pressure chamber base, the second self-balancing piston rod and the pressure chamber base are sealed through a second flange end cover, one end of the second self-balancing piston rod extends to a position below the pressure chamber base, another end of the second self-balancing piston rod extends to a position above the pressure chamber base, and a second linear variable differential transformer (LVDT) displacement sensor is connected between the second self-balancing piston rod and the pressure chamber base; wherein a third self-balancing piston rod is horizontally arranged on a left side part of the pressure chamber barrel, the third self-balancing piston rod and the pressure chamber barrel are sealed through a third flange end cover, one end of the third self-balancing piston rod extends outside the pressure chamber barrel, another end of the third self-balancing piston rod extends into the pressure chamber barrel, and a third linear variable differential transformer (LVDT) displacement sensor is connected between the third self-balancing piston rod and the pressure chamber barrel; wherein a fourth self-balancing piston rod is horizontally arranged on a right side part of the pressure chamber barrel, the fourth self-balancing piston rod and the pressure chamber barrel are sealed through a fourth flange end cover, one end of the fourth self-balancing piston rod extends outside the pressure chamber barrel, another end of the fourth self-balancing piston rod extends into the pressure chamber barrel, and a fourth linear variable differential transformer (LVDT) displacement sensor is connected between the fourth self-balancing piston rod and the pressure chamber barrel; wherein the first self-balancing piston rod and the second self-balancing piston rod are coaxially distributed, and the third self-balancing piston rod and the fourth self-balancing piston rod are coaxially distributed; and wherein hoisting lugs are arranged outside the pressure chamber barrel.

5. The test equipment according to claim 1, wherein a slipway guide sliding block is fixedly arranged on a lower surface of the pressure chamber transfer slipway, and is in sliding connection with the pressure chamber transfer track; wherein a rack is fixedly mounted on a side part of one track of the dual-track structure of the pressure chamber transfer track, and is parallel to the pressure chamber transfer track; wherein a hydraulic motor is vertically mounted on the pressure chamber transfer slipway, a power output shaft of the hydraulic motor faces and extends below the pressure chamber transfer slipway, a gear is fixedly mounted on the power output shaft of the hydraulic motor, and the gear and the rack are meshed.

6. The test equipment according to claim 1, wherein the pressure chamber barrel and base packaging fixture comprises a left half fixture and a right half fixture, each of the left half fixture and the right half fixture comprises a semi-ring jacket, a jacket guide supporting table, a jacket fixing guide rail, a jacket following guide rail, a jacket sliding block and a jacket electric pushing mechanism; wherein the jacket guide supporting table is fixedly arranged on one side of the base platform, the jacket fixing guide rail is horizontally and fixedly mounted on an upper surface of the jacket guide supporting table, and the jacket fixing guide rail is a parallel dual-rail structure; wherein the jacket following guide rail is horizontally and fixedly mounted on an upper surface of the pressure chamber transfer slipway, is a parallel dual-rail structure, and is completely the same as the jacket fixing guide rail in a layout height and a rail gauge; wherein the jacket sliding block is fixedly arranged on a lower surface of the semi-ring jacket, and the jacket sliding block is in sliding connection and cooperation with the jacket following guide rail and the jacket fixing guide rail; wherein the jacket electric pushing mechanism is arranged between the semi-ring jacket and the jacket guide supporting table, and the jacket electric pushing mechanism is used for driving the semi-ring jacket to move in a straight line on the jacket following guide rail and the jacket fixing guide rail; and wherein transverse pressure elbow clamps are respectively arranged on the semi-ring jacket of the left half fixture and the semi-ring jacket of the right half fixture, and the pressure chamber base and the pressure chamber barrel are packaged and fixed through the two semi-ring jackets which are buckled together.

7. A method for the rock true triaxial dynamic compression-shear test equipment under deep complex structure conditions according to claim 1, comprising the following steps:
step I: preparing rock specimens, packaging the rock specimens with mutually-buckled pressure blocks, additionally preparing three sets of linear variable differential transformer (LVDT) displacement sensors, combining the three sets of LVDT displacement sensors with the rock specimens and the mutually-buckled pressure blocks together to finally form a specimen combination, and performing volume change measurement on the rock specimens through respectively using the three sets of LVDT displacement sensors in a large principal stress direction, an intermediate principal stress direction and a minimum principal stress direction;
step II: adjusting the test equipment to an initial state, wherein in the initial state, the pressure chamber base is located at a front station of the counterforce framework, the pressure chamber barrel is located on the pressure chamber barrel lift type bearing table at a rear station of the counterforce framework, and a semi-ring jacket of a left half fixture of the pressure chamber barrel and base packaging fixture and a semi-ring jacket of a right half fixture of the pressure chamber barrel and base packaging fixture are in a separated state;
step III: placing the prepared specimen combination at a top end of a second self-balancing piston rod of the pressure chamber base, and adjusting positions of the three sets of LVDT displacement sensors and an extension quantity of a contact probe on the specimen combination to enable the three sets of LVDT displacement sensors to be within a test measurement range;
step IV: firstly, vertically hoisting the pressure chamber barrel from the pressure chamber barrel lift type bearing table through the pressure chamber barrel hoisting mechanism, then controlling the pressure chamber barrel lift type bearing table to fall down to a lower position, then starting a hydraulic motor, and under a meshing transmission action of a gear and a rack, and enabling the pressure chamber transfer slipway bearing the pressure chamber base and the specimen combination to move along the pressure chamber transfer track until the pressure chamber base moves just below the pressure chamber barrel, so that at the time, a jacket fixing guide rail on a jacket guide supporting table and a jacket following guide rail on the pressure chamber transfer slipway are accurately linked together;

step V: enabling the pressure chamber barrel to fall down onto the pressure chamber base through the pressure chamber barrel hoisting mechanism so that the pressure chamber barrel and the pressure chamber base are buckled together, and at this time, the specimen combination is located inside the pressure chamber barrel, then enabling the suspension arm of the pressure chamber barrel hoisting mechanism and hoisting lugs outside the pressure chamber barrel to be disconnected, and then controlling the suspension arm of the pressure chamber barrel hoisting mechanism to elevate to reset;

step VI: starting a jacket electric pushing mechanism to enable the semi-ring jacket to move, enabling a jacket sliding block at a bottom part of the semi-ring jacket to move to the jacket following guide rail from the jacket fixing guide rail until the semi-ring jacket of the left half fixture and the semi-ring jacket of the right half fixture are completely buckled together, then locking the two semi-ring jackets into a whole through transverse pressure elbow clamps, and then controlling the jacket electric pushing mechanism to reset;

step VII: starting the hydraulic motor again, enabling the pressure chamber transfer slipway bearing the pressure chamber and the specimen combination to move to a test station where the counterforce framework is located, and then pre-clamping the specimen combination in the pressure chamber through cooperation of the first self-balancing piston rod, the second self-balancing piston rod, the third self-balancing piston rod and the fourth self-balancing piston rod on the pressure chamber;

step VIII: firstly filling hydraulic oil into the pressure chamber until minimum principal stress hydraulic pressure loading is completed, then starting the first maximum principal stress actuator, the second maximum principal stress actuator, the first intermediate principal stress actuator and the second intermediate principal stress actuator to apply maximum principal stress and intermediate principal stress to the rock specimens in the specimen combination, then performing a rock true triaxial dynamic compression-shear test, and besides, recording test data;

step IX: after the test is completed, firstly controlling the first maximum principal stress actuator, the second maximum principal stress actuator, the first intermediate principal stress actuator and the second intermediate principal stress actuator to reset, then unloading the minimum principal stress hydraulic pressure and completing hydraulic oil discharge;

step X: starting the hydraulic motor, enabling the pressure chamber transfer slipway bearing the pressure chamber and the specimen combination to move to the rear station of the counterforce framework, firstly releasing locking of the two semi-ring jackets by the transverse pressure elbow clamps, and then controlling the two semi-ring jackets to return to the respective initial positions by the jacket electric pushing mechanisms to complete separation of the two semi-ring jackets;

step XI: controlling the suspension arm of the pressure chamber barrel hoisting mechanism to fall, enabling the hoisting lugs outside the pressure chamber barrel and the suspension arm of pressure chamber barrel hoisting mechanism to be connected together, then controlling the suspension arm of the pressure chamber barrel hoisting mechanism to rise to enable the pressure chamber barrel to rise to a high position, at this time, enabling the pressure chamber barrel and the pressure chamber base to complete separation, and besides, removing the exposed specimen combination from the top end of the second self-balancing piston rod of the pressure chamber base; and step XII: starting the hydraulic motor again, enabling the pressure chamber transfer slipway bearing the pressure chamber base to move to the front station of the counterforce framework, besides, controlling the pressure chamber barrel lift type bearing table at the rear station of the counterforce framework to rise, and finally, enabling the pressure chamber barrel to drop onto the pressure chamber barrel lift type bearing table through the pressure chamber barrel hoisting mechanism.

* * * * *